United States Patent [19]

Hotzel et al.

[11] Patent Number: 5,371,107

[45] Date of Patent: Dec. 6, 1994

[54] USE OF ASCORBIC ACID IN THE GENITAL AREA AND CORRESPONDING MEDICINAL PREPARATIONS

[75] Inventors: Knut A. Hotzel, Luechow; Eiko Petersen, Freiburg, both of Germany

[73] Assignee: Artesan Pharma GmbH, Luechow, Germany

[21] Appl. No.: 172,641

[22] Filed: Dec. 22, 1993

[51] Int. Cl.⁵ .................. A61K 31/375; A61K 9/06
[52] U.S. Cl. ................... 514/474; 514/931; 514/934; 514/967; 514/969
[58] Field of Search ............ 514/474, 967, 931, 934, 514/969; 424/DIG. 14, DIG. 15

[56] References Cited

U.S. PATENT DOCUMENTS

| | | | |
|---|---|---|---|
| 2,918,404 | 12/1959 | Mende et al. | 167/58 |
| 4,049,798 | 9/1977 | Bottomley | 424/195 |
| 4,150,128 | 4/1979 | Jasionowski | 424/240 |
| 4,154,820 | 5/1979 | Simoons | 424/175 |
| 4,211,769 | 7/1980 | Okada et al. | 424/177 |
| 4,318,926 | 3/1982 | Schmidt-Ruppin et al. | 424/330 |
| 4,414,212 | 11/1983 | Naylor | 424/247 |
| 4,424,232 | 1/1984 | Parkinson | 424/279 |
| 4,434,159 | 2/1984 | Seking et al. | 424/178 |
| 4,585,792 | 4/1986 | Jacob et al. | 514/274 |
| 4,670,263 | 6/1987 | Noorlander | 424/195.1 |
| 4,696,917 | 9/1987 | Lindstrom et al. | 514/54 |
| 4,711,780 | 12/1987 | Fahim | 424/145 |
| 4,722,936 | 2/1988 | Jacob | 514/274 |
| 4,914,131 | 4/1990 | Haines et al. | 514/626 |
| 4,937,234 | 6/1990 | Fahim | 514/53 |
| 4,943,433 | 7/1990 | Rudov | 514/474 |
| 5,032,610 | 7/1991 | Borretzen | 514/467 |
| 5,089,508 | 2/1992 | Burzynski | 514/328 |
| 5,132,101 | 7/1992 | Vogel et al. | 514/410 |
| 5,135,948 | 8/1992 | Borretzen et al. | 514/467 |
| 5,179,120 | 1/1993 | Vogel et al. | 514/410 |
| 5,244,902 | 9/1993 | Sharpe et al. | 514/270 |
| 5,244,922 | 9/1993 | Burzynski | 514/561 |

FOREIGN PATENT DOCUMENTS

| | | |
|---|---|---|
| 0046409 | 2/1982 | European Pat. Off. . |
| 527241 | 2/1993 | European Pat. Off. . |
| 2646604 | 5/1989 | France . |
| 8704069 | 7/1987 | WIPO . |
| 8804176 | 6/1988 | WIPO . |

OTHER PUBLICATIONS

JP-A-61 65 822, Patent Abstracts of Japan, vol. 10, No. 230, (c–365)[2286]; Aug. 8, 1986, p. 111 C 365.

Rote Liste, 1987, Editio Cantor, Aulendorf, Germany, No. 45 126 and 45 127.

S. L. Romney, et al, "Plasma Vitamin C and Uterine Cervical Dysplasia", American Journal of Obstetrics and Gynecology, vol. 151, No. 7, Apr. 1, 1985, pp. 976–980.

B. Hoffmann, et al, "The Vitamin C Concentrations in the Cervical Mucous in Women Infested and Uninfested by Trichomonas Vaginalis"; Ginekologia Polska, vol. 40, No. 7, 1969, pp. 773 to 778.

*Primary Examiner*—Shep K. Rose
*Attorney, Agent, or Firm*—Richard S. Roberts

[57] ABSTRACT

A method of treating conditions of amine vaginitis, purulent vaginitis and dysplasia of the mouth of the uterus resulting from papilloma virus infection in the genital region of female animals by topically applying ascorbic acid to the affected region. The invention also provides a medicinal composition in the form of a an ointment or tablet containing about 3% to about 50% by weight of ascorbic acid and the balance a pharmaceutically acceptable ointment or tabletting carrier.

9 Claims, No Drawings

USE OF ASCORBIC ACID IN THE GENITAL AREA AND CORRESPONDING MEDICINAL PREPARATIONS

BACKGROUND OF THE INVENTION

The present invention relates to the use of ascorbic acid, as well as ascorbic acid containing medicaments.

Ascorbic acid is well known in the art (cf. Roempp, Chemielexikon, 9th extended and revised edition, vol. 1, 1989 pg. 265, ff.) In the medical field, the typical C-avitaminosis is scurvy from which the name ascorbic acid is derived. Therapeutically, vitamin C is used for the prophylaxis and combatting of scurvy, following operations, assisting the resorption of orally administered iron, for the faster healing of bone fractures, and as a general tonic. Higher vitamin C doses are recommended as a preventative against catching colds, for speeding up the healing of wounds, and for the treatment of rheumatism and polyarthritis.

Ascorbic acid is used as an antioxidant for technical purposes and also finds use in the foods sector. The useability of high ascorbic acid doses against colds and cancer is still subject to doubt. However, it has positive effects on the healing of wounds and the immune system.

Although ascorbic acid/vitamin C has been known for decades, hitherto only inadequate information exists regarding the use thereof in the gynecological field (see patent applications WO-A-87/04069 and WO-A-88/04176). In the American Journal of Obstetrics and Gynecology, 151 (7), Apr. 1, 1985, pp. 976 to 980, the C. B. Mosby Company, St. Louis Miss., it is stated that asymptomatic patients, who have been cytologically proved to have a dysplasia of cervical epithelial cells, have a reduced vitamin C content in the plasma. Mention is also made therein of the fact that further research is required because the link between the plasma concentration and different epithelial dysplasia is far from clear. Reference is made to further studies which support a link between vitamin C level in the plasma and dysplasia and which are given in order to update the subject of vitamin C and dysplasia. The report ends with still outstanding questions and calls for further research. This document does not refer to the local application of vitamin C to the vagina and the mouth of the uterus and in no way makes this obvious.

Since in animals and in humans particularly, the most varied ailments and illnesses occur in the genital region, there is a considerable need for a simple medicament or formulation which can provide assistance in this connection. Surprisingly, this is made possible by the present invention with the use of topically applied ascorbic acid.

SUMMARY OF THE INVENTION

The invention provides a method of treating conditions of amine vaginitis, purulent vaginitis and dysplasia of the mouth of the uterus resulting from papilloma virus infection in the genital region of female animals which comprises topically applying ascorbic acid to the affected region in an amount and for a time sufficient to cause a substantial reduction of such condition.

The invention also provides a medicinal ointment composition which comprises from about 3% to about 50% by weight of the composition of ascorbic acid and the balance a pharmaceutically acceptable ointment carrier. In addition the invention provides a medicinal composition in the form of a tablet which comprises from about 3% to about 50% by weight of the composition of ascorbic acid and the balance a pharmaceutically acceptable tabletting carrier.

DETAILED DESCRIPTION OF THE PREFERRED EMBODIMENT

It has been found that several illnesses in the genital region can now be effectively treated according to the present invention. One such illness is dysplasia in the mouth of the uterus due to papilloma virus infections. It is known that smoking is one of the risk factors for the occurrence of genital cancer. This is possibly linked with a relative deficiency of vitamin C in smokers because they have a 40% higher need for vitamin C than non-smokers. Research carried out on a patient with severe dysplasia of the cervix (Pap. IV) led to a normalization of the cytological smear (Pap. II) after vitamin C treatment according to the invention. At the same time, the condyloma caused by papilloma viruses and the inflammation reaction on the cervix disappeared. In other cases, disturbances to vaginal flora (e.g. amine vaginitis) was reversed in cases in which the normal lactobacillus flora by Gardnerella vaginalis, anaerobes and other bacteria was suppressed. Bacterially disturbed vaginal flora with an unpleasant smelling discharge is frequently encountered and roughly 10% of women suffer from this apparently aesthetic problem. Due to the high bacterial count of potential pathogenic bacteria, there is additionally an increased inflammation risk during pregnancy, following operations, or due to sexually transmitted pathogenic organisms which are able to enter the internal genital region and trigger infections there. Research up to now has shown that this bacterial discharge cannot always be eliminated by the various medicaments which are used both perorally and locally. In addition, due to a weakness of the individual normal flora, this problem very rapidly reoccurs in many women. Therefore treatment possibilities have been sought which can be used in a repeated manner while being well tolerated by the patient. It is known that through the acidification of the vaginal region, the normal flora are aided to such an extent that in many cases this brings about a normalization of the vaginal flora. Research with the administration of vitamin C according to the invention in tablet form to the vagina having such bacterial problems has revealed that this can normalize the vaginal flora. This treatment is very well accepted by the patient. In vitro research has supported the clinical observation that normal flora, i.e. lactobacilli are less inhibited under vitamin C than other bacteria, e.g. intestinal bacteria.

The invention is also useful for the treatment of purulent vaginitis, or inflammation of the vagina, for which up to now no typical pathogenic organism has been identified and which is probably caused by a virus infection. Purulent vaginitis is an as yet unsolved problem which is a very considerable burden to young patients who it generally affects. Specific pathogenic organisms for this disturbance have not as yet been identified and it is possibly a virus infection. There is generally a disturbance of the vaginal flora. The local use of vitamin C according to the invention acts both against the virus infection with activation of the immunodefense, and the elimination of the potential pathogenic bacteria by acidification. Long term use of vitamin C according to the process of the invention by women suffering from this disturbance has led to a considerable improvement even extending to complete healing. The patient who has frequently suffered from this illness for years tolerates the therapy well even when it lasts several weeks. For the various fields of application different doses are required. On the one hand, an activation of the humoral and cellular defense is intended when eliminating virus infections, while on the other hand, in the case of bacterial disturbances, acidification and inhibition of the bacteria must not be so pronounced that flora cannot grow. However, the minimum dose of ascorbic acid should not drop below approximately 3% by weight of the overall composition and the maximum dose of ascorbic acid should not exceed approximately 50% by weight of the overall composition, preferably and from about 10% to about 20% by weight ascorbic acid. Advantageously, there are different vitamin C concentrations between 50 and 500 mg per tablet or gram of ointment. The use time differs for the different indications, in the case of purulent vaginitis and papilloma virus infection, therapy over several weeks is necessary. In one form of the invention, the therapeutic composition is a medicinal ointment composition. Such an ointment can contain a pharmaceutically acceptable ointment carrier comprises one or more component selected from the group consisting of paraffin, a $C_{12}$ to $C_{24}$ fatty alcohol and petroleum jelly. A preferred overall composition contains from about 10% to about 20% by weight ascorbic acid, from about 30% to about 50% by weight highly liquid paraffin, from about 20% to about 30% by weight cetyl stearyl alcohol and from about 15% to about 25% by weight white petroleum jelly. One particularly preferred ointment composition contains about 12.5% by weight ascorbic acid, about 39.4% by weight highly liquid paraffin, about 26.3% by weight cetyl stearyl alcohol and about 21.8% by weight white petroleum jelly. In another form of the invention, the therapeutic composition is a medicinal tablet composition. Such can comprise from about 3% to about 50% by weight of the composition of ascorbic acid and the balance a pharmaceutically acceptable tabletting carrier comprising one or more components selected from the group consisting of glucose, cellulose powder, polyvinyl pyrrolidone and magnesium stearate. A preferred tablet comprises from about 5% to about 10% by weight of ascorbic acid, from about 80% to about 90% by weight glucose 1 $H_2O$, from about 2% to about 10% by weight cellulose powder, about 1% by weight polyvinyl pyrrolidone, and about 1% by weight magnesium stearate. One preferred composition comprises about 89% by weight glucose 1 $H_2O$, about 4% by weight cellulose powder, about 1% by weight polyvinyl pyrrolidone, and about 1% by weight magnesium stearate. The local use of vitamin C in patients with these problems offers several advantages. Through local application, a high vitamin C concentration is achieved at the site where it is required. The vitamin C deficiency of dysplastic cells can possibly be eliminated and as a result a protective effect against further cancer development is obtained. The local application can be done by the patient so that longer uses are more easily possible. The long term acidification of the vaginal region favors the selection and colonization of important types of normal flora, i.e. lactobacillus. Vitamin C is completely atoxic and can be administered in high concentrations since no overdoses are known. Patients have a very high tolerance for the long term application of vitamin C. A systematic absorption of vitamin C from the vaginal region is desired and additionally leads to an increased vitamin C supply. These are no objections to vitamin C administration during pregnancy.

The following non-limiting examples serve to illustrate the invention.

EXAMPLE 1

A 12.5% by weight vitamin C containing vaginal ointment is produced in a 200 kg batch in the following manner. The following components are melted in an ointment machine (dissolver) at 80° C.:

| | |
|---|---|
| White vaseline (petroleum jelly) | 43,750 g |
| Cetyl stearyl alcohol (Lanette N) | 52,500 g |
| Highly liquid paraffin | 78,750 g |

The melt is stirred and homogenized for 20 minutes and cooling is allowed to start. The dissolver is switched off at an internal temperature of 35° C. At an internal temperature of 30° C., 25,000 g of ascorbic acid are added and the dissolver is allowed to run for 15 minutes. The mixture is cold stirred in a partial vacuum and then is introduced into a storage container via a homogenizer.

EXAMPLE 2

A 5% by weight vitamin C containing tablet is produced in the following manner for a batch size of 100,000 tablets (100 kg). The following components are fine screened (Frewitt screening machine) to a 1.0 mm mesh size and mixed for 10 minutes in a tumbling drum mixer in a V2A high grade steel container (200 liters):

| | |
|---|---|
| Ascorbic acid | 5,000 g |
| Glucose 1 $H_2O$ | 89,000 g |
| Cellulose powder (tabletting aid K) | 4,000 g |
| Poly(1-vinyl-2-pyrrolidone 25,000 (Kollidone 25) | 1,000 g |

Thereafter, 1,000 g of magnesium stearate are then screened in by hand and mixed for two minutes in the tumbling drum mixer.

EXAMPLE 3

A 21 year old patient in the seventeenth week of her second pregnancy is diagnosed with amine vaginitis (bacterial vaginosis). Symptoms include vaginal odor and discharge. The risk to the patient is premature childbirth. Found is a thin discharge having a pH value of 5.2, and which tests KOH positive. Microscopic evaluation shows clue cells which are large quantities of bacteria with little morphologic difference. Microbiological culture: Gardnerella vaginalis—$10^7$ nuclei/ml, bacteroides—ssp. $10^7$/ml, peptococci—$10^7$/ml vaginal secretion, lactobacillus—ssp. $10^4$/ml. Therapy is one daily vaginal tablet of vitamin C having 250 mg ascorbic acid for ten days. An examination after two weeks shows no further complaints, normal flow, pH of 4.0, KOH tests negative, microscopic lactobacillus flora. Culture results: lactobacillus jensenii—$10^7$/ml.

EXAMPLE 4

A 35 year old patient is observed with distinctive superficial condyloma of the cervix (portio). Cytology: Pap IV, a severe dysplasia. Histology: koilocytosis. Therapy: one daily tablet of vitamin C having 250 mg ascorbic acid topically to the affected area over a total of four months. An examination after two months shows: clinically—a transformation zone with no more surface condyloma; cytology—Pap II, no more dysplasia. An examination after eighteen months shows: clinically—inconspicuous; cytology—Pap II, no more dysplasia.

What is claimed is:

1. A method of treating conditions of amine vaginitis, purulent vaginitis and dysplasia of the mouth of the uterus resulting from papilloma virus infection in the genital region of female animals which comprises topically applying a composition consisting of a pharmaceutically acceptable carrier and ascorbic acid to the affected region in an amount and for a time sufficient to cause a substantial reduction of such condition.

2. The method of claim 1 wherein the ascorbic acid is contained in a tablet or ointment.

3. The method of claim 1 which comprises applying a medicinal ointment composition to the affected area which comprises from about 3% to about 50% by weight of the composition of ascorbic acid and the balance a pharmaceutically acceptable ointment carrier.

4. The method of claim 3 wherein the pharmaceutically acceptable ointment carrier comprises one or more components selected from the group consisting of paraffin, a $C_{12}$ to $C_{24}$ fatty alcohol and petroleum jelly.

5. The method of claim 3 wherein the medicinal ointment composition comprises from about 10% to about 20% by weight ascorbic acid, from about 30% to about 50% by weight highly liquid paraffin, from about 20% to about 30% by weight cetyl stearyl alcohol and from about 15% to about 25% by weight white petroleum jelly.

6. The method of claim 3 wherein the medicinal ointment composition comprises about 12.5% by weight ascorbic acid, about 39.4% by weight highly liquid paraffin, about 26.3% by weight cetyl stearyl alcohol and about 21.8% by weight white petroleum jelly.

7. The method of claim 1 which comprises applying a medicinal composition in the form of a tablet to the affected area which comprises from about 3% to about 50% by weight of the composition of ascorbic acid and the balance a pharmaceutically acceptable tabletting carrier comprising one or more components selected from the group consisting of glucose, cellulose powder, polyvinyl pyrrolidone and magnesium stearate.

8. The method of claim 7 wherein the medicinal composition comprises from about 5% to about 10% by weight of ascorbic acid, from about 80% to about 90% by weight glucose 1 $H_2O$, from about 2% to about 10% by weight cellulose powder, about 1% by weight polyvinyl pyrrolidone, and about 1% by weight magnesium stearate.

9. The method of claim 7 wherein the medicinal composition comprises about 89% by weight glucose 1 $H_2O$, about 4% by weight cellulose powder, about 1% by weight polyvinyl pyrrolidone, and about 1% by weight magnesium stearate.

* * * * *